Figures 1, 2, 3, 4, 5:
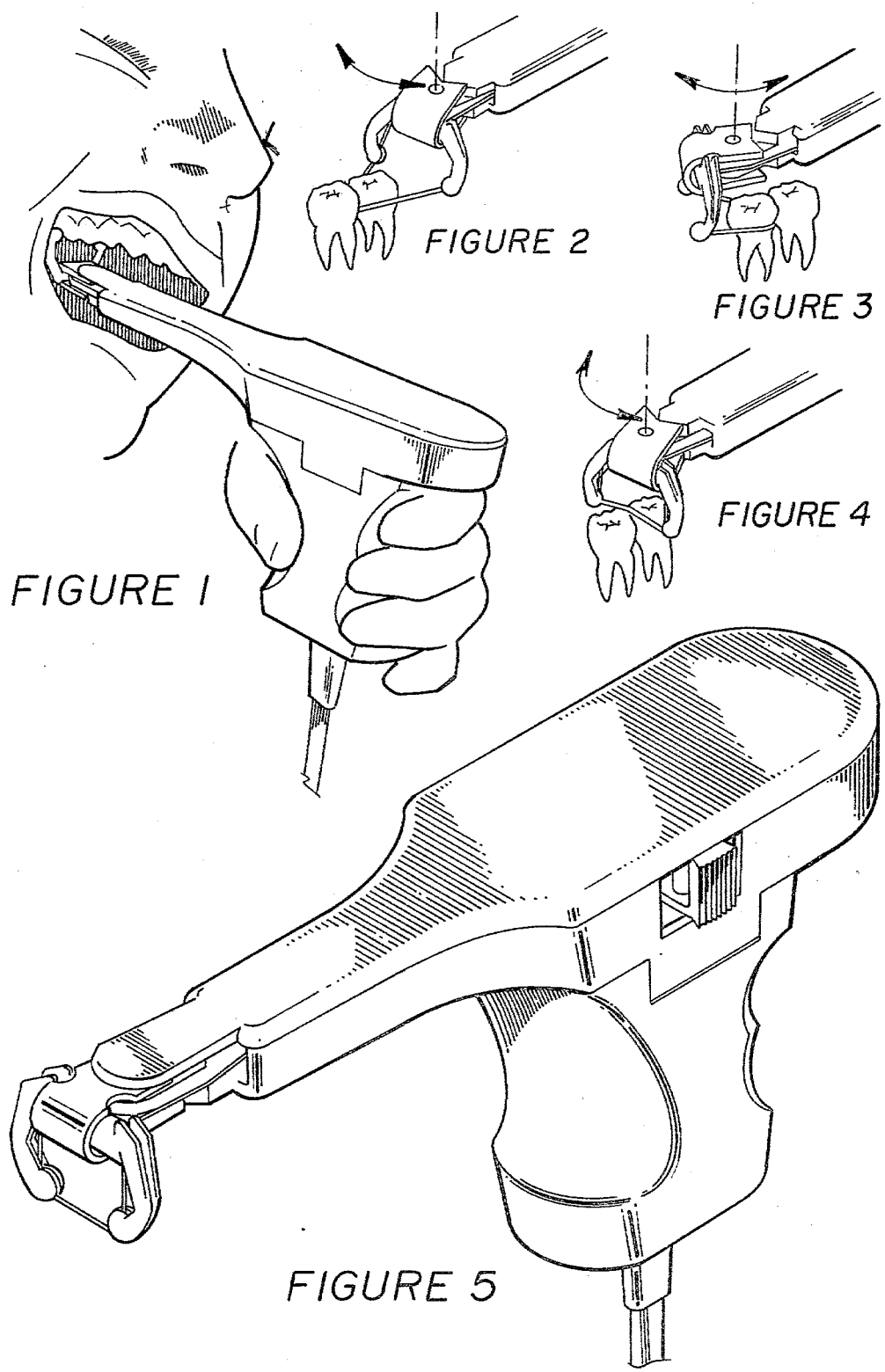

United States Patent [19]

Lecouturier

[11] 4,245,658
[45] Jan. 20, 1981

[54] AUTOMATIC FLOSSING APPARATUS

[76] Inventor: Jacques M. Lecouturier, 350 Holly Dr., San Rafael, Calif. 94903

[21] Appl. No.: 28,365

[22] Filed: Apr. 9, 1979

[51] Int. Cl.³ .............................................. A61C 15/00
[52] U.S. Cl. ................................................. 132/92 A
[58] Field of Search ................... 132/92 A, 92 R, 91, 132/DIG. 2

[56] References Cited

U.S. PATENT DOCUMENTS

| 691,581 | 1/1902 | Baumeister | 132/91 |
| 924,543 | 6/1909 | Dysart | 132/92 A |
| 1,417,518 | 5/1922 | Henerlau | 132/92 R |
| 1,534,171 | 4/1925 | Fickes | 132/91 |
| 1,666,877 | 4/1928 | Cummer | 132/92 R |
| 3,106,216 | 10/1963 | Kirby | 132/92 R |
| 3,667,483 | 6/1972 | McCabe | 132/92 A |
| 3,734,107 | 5/1973 | Thierman | 132/92 A |
| 3,847,167 | 11/1974 | Brien | 132/92 R |
| 4,005,721 | 2/1977 | Yasumoto | 132/91 |
| 4,031,908 | 6/1977 | Ting | 132/91 |
| 4,094,328 | 6/1978 | Ray | 132/91 |

Primary Examiner—Gene Mancene
Assistant Examiner—John J. Wilson

[57] ABSTRACT

This is a flossing apparatus that stores dental floss, holds it automatically under tension and agitates and renews the floss during its manipulations. The floss unwinds from one spool and rolls on another automatically. The floss makes a complete circuit passing by an oscillator imparting back and forth movements to the floss and subsequently to a two-pronged headpiece holding the floss under tension across the two prongs. The spools are connected by a clutch and crank transmission mechanism which maintains controllable floss tension.

13 Claims, 8 Drawing Figures

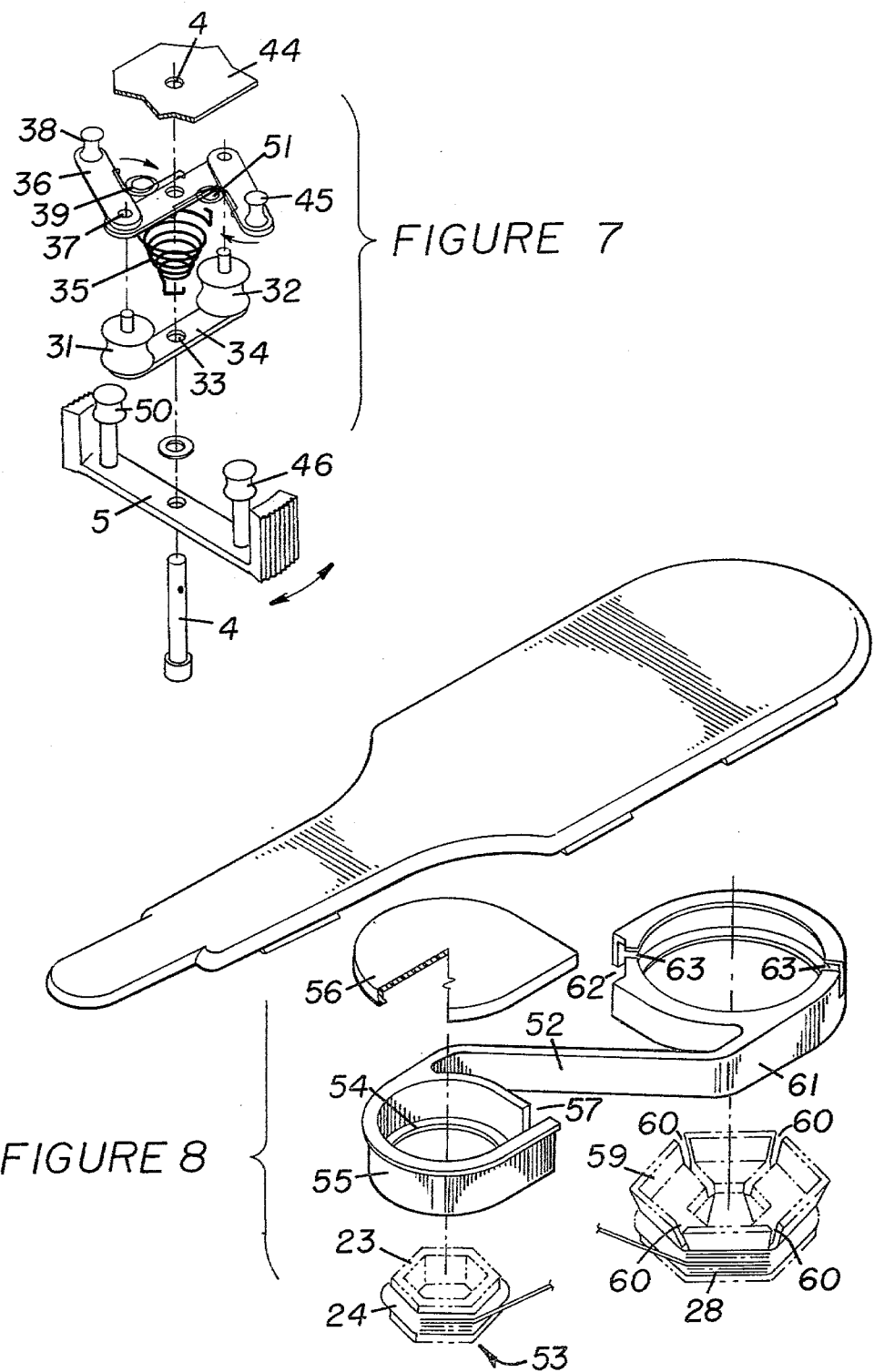

AUTOMATIC FLOSSING APPARATUS

REFERENCE CITED; UNITED STATES PATENT:

U.S. Pat. No. 3,621,853, G. H. Montalbo, Nov. 23, 1971,
U.S. Pat. No. 3,667,483, McCabe, June 6, 1972,
U.S. Pat. No. 3,734,107, Thierman, May 22, 1973,
U.S. Pat. No. 3,792,706, A. E. Keese, Feb. 19, 1974,
U.S. Pat. No. 3,847,167, Brien, Nov. 12, 1974,
U.S. Pat. No. 4,005,721, Yasumoto, Feb. 1, 1977,

STATE OF THE ART

The apparatuses now available on the market are primarily limited to providing tension in the floss. While some tension is desirable to move the floss between the teeth, undue tension is most often required by these apparatuses to prevent the floss from slipping off its handle. Undue floss tension makes it difficult to insert the floss between tight teeth and even more difficult to remove it from the same spot.

The typical floss consists of many unworn strands. Placing or removing the floss between tight teeth is better handled by moving the floss laterally between the teeth while exerting a soft downward pressure. In this manner each strand of the floss traverses the space between the tight teeth individually. Undue pressure, either downward or upward only forces all the strands to cross the tight spot at once and makes it even more difficult.

Several hundred patents have already been granted on various flossing apparatuses which illustrate the need for such devices while their appearance on the market place testifies for their appeal.

The basic two-pronged fork design inception took place at the turn of the century. The problems to be tackled are numerous and many were solved in many ingenious ways by my predecessors. These problems are:
1. To hold the floss in a tense situation.
2. To clamp down one end of the floss section to be used in the flossing operation.
3. To clamp down the other end.
4. To limit the waste of floss.
5. To conveniently renew the useful floss portion.
6. To agitate properly the useful floss portion.
7. To guide the floss intoa slip-free track.
8. To provide a container for the floss.
9. To provide a cutter to dispose of the floss.
10. To be able to reduce the floss tension for certain types of flossing needs.
11. To make all these operations as mechanical as possible.

BACKGROUND OF THE INVENTION

In the opinion of the dental profession, most problems with adult teeth are the result of deposits that are accumulated on the tooth's enamel. While regular tooth brushing removes these deposits (also called plaque) on the upper and side sections of the teeth, it is inefficient to dislodge these plaque from the teeth interstices. These deposits between the teeth and at the neck of the tooth become the most common cause for cavities and gum deterioration.

Teeth flossing is universally recognized by dentists as the only effective method to prevent decays and gum infections of the back teeth.

Flossing which was commercially introduced several decades ago has not gained the social acceptance of brushing as a regular and necessary hygiene operation.

One of the reasons that may explain this lack of individual participation in a recognized form of preventive dental care may lay in the actual unpracticality of the flossing operation as it has to be conducted with present available means.

There are obvious hindrances to inserting one's fingers in one's mouth. Practice is needed to learn the position of the teeth interstices. Patience is required to obtain the proper tension in the floss and to repeat each preparatory operation when the floss becomes frayed, soiled or slippery. Many persons are handicapped by their lack of dexterity. The hands have to be washed before each operation.

Persons conscious of the irreplaceable advantages conferred by a healthy set of teeth find it necessary to visit a dental hygienist twice a year to supplement the insufficiency of tooth brushing at a cost of from $15.00 to $25.00 per visit; notwithstanding the fact that persons aware of the benefits of regular visits to their hygienist are among the most dedicated teeth brushers.

In a lifetime the average person spends several hundred dollars to repair damages done to their teeth mostly to the interstices and neck regions of the molars and premolars and unquestionably as a consequence of the limitations of tooth brushing.

The availability of an elaborate apparatus to reduce dental repair costs appear a worthy investment.

The predominate criteria in the conception of this invention was capacity for performances. Dentists seemed unanimous in the opinion that patients have difficulties in taking sufficient care of their teeth.

The proposed invention attempts to bridge a gap between the highly technological dental care provided by the dentist and the primitive tools offered to the individual for private dental hygiene.

OBJECTS OF THE INVENTION

The invention has for its purpose to improve by speed, convenience and results, all the flossing operations normally performed by hand or existing apparatus. Once the new spool of floss is installed and the floss wired on its circuit, and once the user places the apparatus in the proper positions the flossing operation can be considered automatic.

One object of the apparatus is to agitate the floss in such a manner that it performs its cleaning action by rubbing the periphery of the tooth in a number of ways. Such variety of motions being necessary to properly floss between the teeth and around the neck of the tooth.

Another object is to continuously renew the portion of the floss at work to utilize more efficiently the cleaning agent incorporated in the floss.

Another object is to have the mechanism automatically develop the predetermined tension in the floss which can be regulated by the operator, then to maintain this tension at the satisfactory level whenever other factors tend to disrupt it.

Another object is to allow the operator to utilize lower tension levels for the performance of operations associated with the curving of the floss around the neck of the tooth.

Another object is to ease the insertion and removal of the floss between tight teeth. This ease is afforded by the constant lateral motions of the floss as it is being pressed downward or upward to traverse the tight intervals between the teeth.

Another object of the invention is to eliminate floss breaking by not allowing fraying to develop in one spot.

Another object of the invention is to limit how deep the floss can drop between the teeth.

Another object is to eliminate hand contact with the floss once a new spool has been installed and to automatically store the used floss in a closed container.

Another object is to simplify the refilling of the automatic flosser apparatus by providing the floss in a cartridge which is the container for both the new and used floss. The floss cartridge being disposable units to be purchased and then discarded after use.

Another object is to allow for interchangeably mounting rubbery cushions between the prongs. These cushions are designed to massage the gingiva on both sides of the teeth and to subsequently stimulate the gum tissues.

Another object is to eventually incorporate a water jet with one or two nozzles to be located between the prongs and further complement the cleaning operation.

Another object is to provide the user with a flossing apparatus leaving an unobstructed vision of the mouth inside as the flossing takes place while said vision of the mouth inside can be improved by the adjunction of accessories such as a magnifying mirror or a light bulb that would better reveal the details of the teeth configuration; the object here being to design the object to make the support of these accessories feasible.

Another object is to have an apparatus with the smallest possible headpiece to insert inside the mouth in order to create the least possible discomfort while at the same time offering the maximum of reach and motions.

Another object is to have an apparatus compact in size and versatile in flossing, always loaded and ready for use, while preserving the floss from contamination.

Another object is to have an apparatus adaptable to all categories of users and for all types of flossing needs.

SUMMARY OF THE INVENTION

This is an apparatus which holds dental floss under tension in a circuit that begins with a disbursing spool of new floss, winds across two prongs and ends around a second receiving spool which rolls up the used floss in a closed housing.

A mechanism transmits the floss rotation of one spool to the other, while a crank insures that the floss can only transfer in one direction. The floss transfer is implemented by action on the floss through an oscillator. The spool receiving the floss turns faster than the disbursing spool which causes increased tension in the circuit of the floss as it transfers. As the floss tension reaches an apex the spools disconnect causing the floss to be released which diminishes the floss tension until continuous floss transfer brings the floss tension to a new apex under which the process starts over again.

The oscillator makes the floss circuit go back and forth in short movements. The floss under tension causes the same movements to be carried to the prongs which in turn oscillate concurrently with the action of taut floss across the prongs.

ILLUSTRATIONS:

FIG. 1: Apparatus with motor in operation.

FIGS. 2, 3 & 4: Positions of the floss across the prongs.

FIG. 5: The motor-driven apparatus at rest.

Figure 6:
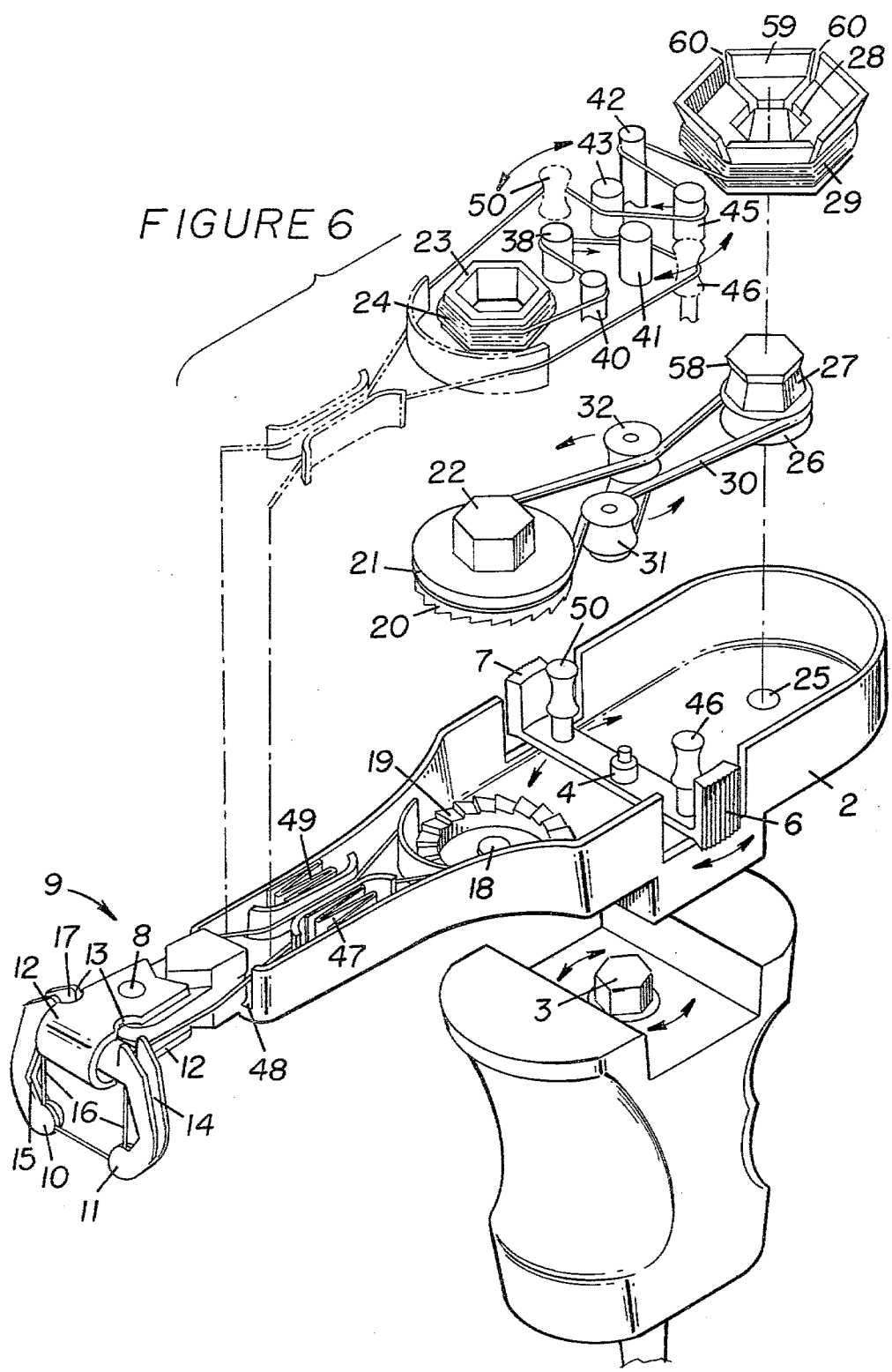

FIG. 6: Exploded view of the apparatus.

FIG. 7: Mechanism responding to floss tension acting as a clutch on the pulley of the transmission mechanism between the spools.

FIG. 8: View of the cartridge containing the spool of fresh floss and the spool rolling up the used floss.

DESCRIPTION OF THE INVENTION IN ITS PREFERRED EMBODIMENT

The invention (FIGS. 1 and 5) is an apparatus with a two-pronged oscillating and reversible headpiece for the automatic manipulation of dental floss between the teeth.

In (FIG. 2), the dental floss across the prongs is seen in its position, displaced in a jigsaw manner against the back wall of a molar.

In (FIG. 3), the same type of flossing motion takes effect against the front wall of the molar.

In (FIG. 4), the floss is in a straight line across the prongs and under maximal tension for easy penetration or removal of the floss between the interstices of two teeth. As the user presses the floss down or lifts it up, the floss is subject to lateral motions that are conductive to an easy and swift insertion or removal of the floss.

The floss section across the prongs is subject to a number of motions. These motions are:

a. Concurrent oscillations and jigsaw motions when the floss is in a straight line.

b. Jigsaw motions when the floss is curved around a tooth.

c. Minute jerky displacements within the other motions described described above in a. and b. These displacements occurring as a result of incessant and minute changes of tension level in the floss.

d. Continuous renewal of the floss in a unilateral motion.

e. Upward and downward motions against the walls of the teeth at the election of the user.

The exploded view of the apparatus in (FIG. 6) shows the various parts of the apparatus.

A casing (1) contains the motor which is either electric or mechanical. Over the motor is attached the body (2) of the apparatus.

The apparatus is functional without the motor.

The motor by a cam produces oscillations to the driving part (3). To hook up the motor to the body the male driving part (3) fits into a corresponding female part underneath the axis (4). The motor causes the transversal bar (5) to oscillate. The oscillation of the transversal bar can also be produced manually by the holder of the apparatus by exerting back forth finger motions on the end tips (6) and (7) of the oscillating bar. The body extension supports with a pivot (8) the oscillating headpiece (9). The headpiece supports the reversible prongs (10) and (11). The transversal rod that unites the prongs is hinged inside the U-shaped support (12) allowing the prongs to be moved together upward or downward. The U-shaped support (12) supporting the prongs is carved with four notches. These notches are located in a vertical plane of the transversal rod uniting the two prongs. Two of these notches are shown in (13) while their symmetrical opposite notches are not visible on the drawing and are occupied by the prongs.

The prongs are carved with longitudinal grooves (14) and (15). These grooves may actually traverse the prongs completely in their center section allowing the floss to appear inside the prongs in (16). The floss enters either groove from opening (17) or the opposite opening. Once the floss is engaged in the prongs, the prongs can be flipped upward or downward without having to reposition the floss.

Tension in the floss causes the tips of the prongs to bend towards one another. This bent position insures that the prongs are further locked into their corresponding notches. When the prongs are aimed upward to clean the upper teeth as in (FIG. 1), they are locked into notches (13). To flip the prongs in their downward positons, the user pushes on the prongs to overcome the floss tension and disengage the prongs from their locking notches. Aimed downward to clean the lower teeth as in (FIG. 6), the prongs are locked within the lower notches not visible on the drawing.

The body of the apparatus supports the two spools. The lower end of the axis of the spool of fresh floss bits over (18). The stationary part of a crank (19) is united to the frame. The corresponding and rotative part of the crank (20) is united to a grooved pulley wheel (21) which in turn holds the polygoned axle (22).

Over said axle 22 bits the hollow and corresponding polygoned shaft (23). Around the shaft is rolled the new floss (24). The lower end of the axis of the spool rolling up the used floss engages into support (25) and supports the grooved pulley-wheel (26) which is smaller than wheel (21). The grooved pulley-wheel (26) supports the polygoned axle (27). Over axle 27 fits the hollow and corresponding polygoned shaft (59). The shaft rolls up and stores the used floss (29).

The transmission of rotation from one spool to the other is in the illustrated embodiment of the invention assumed by a belt (30). Other modes of transmission are feasible. Alternates modes can be carried out with gears or contact wheels.

The belt (30) transmits in one intended direction the rotation of axle (22) to axle (27). The rotational direction of shaft (23), united to axle (22), is transferred by the belt into the rotation of axle (27) united to shaft (28). The crank (20) limits the rotation fo axle (22) to the one intended direction. This process insures that the spool of new floss can only unwind its new floss and is prevented from rolling it back. When the belt (30) is under tension, the axle (27) is also limited to rotate in one direction. This process insures that the shaft of used floss (28) cannot let go the used floss after it has been rolled up. However, it is obvious that should the belt (30) become lax and the transmission of rotation between the spools interrupted, the axle (27) is set free to spin on its axis and can at this time let go of the used floss rolled up on shaft (28).

The belt (30) is kept under tension by two pressure grooved wheels (31) and (32). (FIG. 7) shows that the pair of pressure wheels (31) and (32) mounted on the joining bar (34) can oscillate on the pivot (33). A tension breaker spring (35) presses the pressure wheels against the belt and keeps it under tension. The same process can function with only one pressure wheel.

Pivotable bar (36) mounted at one end of an axis (37) shares the same axis with pressure wheel (31). At the other end of pivotable bar (36) is mounted an extension which becomes the floss tension guider (38). The floss guider (38) can swing toward joining bar (34) while a floss circuit subtension spring (39) offers a resistance to prevent the floss tension guider (38) from swinging freely toward joining bar (34).

In (FIG. 6) the four floss circuit guiders (40), (41), (42) and (43) are stationary and affixed onto a platform separating the spools from the transmission mechanism. This platform is shown partially at (44) in (FIG. 7).

The floss guider (38) in (FIG. 6) swings toward the floss circuit guider (41) when the floss tension overcomes the force of subtension spring (39). In the same manner the floss tension guider (45) moves toward the floss circuit guider (43) when floss tension overcomes the force of subtension spring (51).

The illustration of the floss guiders is simplified to show already the function of each of these guiders. A more elaborate design can be easily visualized to provide the user with a mistake proof channel to wire the floss on its circuit. The circuit of the floss takes the following path: From shaft (23) around stationary floss circuit guider (40), around movable floss tension guider (38), around stationary floss circuit guider (41), around the oscillating guider (46) of the oscillator (5) from where the floss follows a channel inside the body frame, passes over another subtension spring (47), comes out of the body frame from slot (48), enters prong (11) from the upper opening of groove (14), passes inside the prongs in (16), traverses the space across the prongs, enters the groove (15) of the opposite prong (10), comes out of the prongs from the upper opening (17) of groove (15), reenters the body frame, passes over subtension spring (49), follows a channel inside the body frame and goes around the oscillating guider (50) of the oscillator (5), around the stationary floss circuit guider (43), around the movable floss tension guider 45, around satisfactory floss circuit guider (42) to end around shaft (28) which rolls up the floss and stores it.

The floss circuit is submitted to back and forth motions in this particular embodiment of the invention by the oscillating guiders (46) and (50) of the oscillator (5). The back and forth motions of the floss under tension cause the headpiece to oscillate on its pivot. In a different embodiment of the invention, these back and forth motions of the floss could also be applied directly on the headpiece (9) or by an additional mechanism that will impart such back and forth movements of the floss on the floss itself in one convenient location of the floss circuit.

When axle (22) rotates in the direction allowed by crank (20), the rotation of axle (22) is carried by the belt (30) to axle (27).

Wheel (26) is smaller than wheel (21). Shaft (28) is larger than shaft (23). This situation establishes that shaft (28) always wants to roll more floss than shaft (23) can unwind. This process insures that the floss circuit will always be under increasing tension.

The advance of the floss or in other words, the transfer of the floss from shaft (23) to shaft (28) can be implemented by different means. One process implied in the present embodiment of the invention is to force the floss to slide over the supporting parts delineating the floss circuit. To force the floss to slide, the arc courses described by the oscillating guiders (46) and (50) of the oscillator (5) are longer than the arc courses described by the oscillating prongs (10) and (11). In this process, the oscillator, with each alternate swing advances the floss by an increment equal to the discrepancy between the longer arc course of the oscillator over the shorter arc course of the prongs. With one swing, the oscillator pulls the increment of floss off the shaft (23) while in the same time, by action of belt (30) the increment is rolled over shaft (28). With the alternate swing of the oscillator, the crank (20) through the action of the belt (30) prevents the floss on shaft (28) from rolling back to shaft (23) and in this sequence of motions the floss is forced to slide over the prongs by the increment.

In addition to this automatic advance/transfer of the floss that takes place with each alternate swing of the oscillator, the manipulation of the instrument between the teeth also creates a complementary process of floss transfer. This complementary process is generated by a pulling action on the floss section across the prongs when the user pulls on the floss. The elongation of the length of the floss section across the prongs follows the pulling action by the user once the spools are set to release their floss. Consequently an amount of floss is drawn from both spools. The amount drawn from the pick-up spool is eventually rerolled but the amount drawn from the disbursing spool continues into the floss circuit and advances the floss. By this process, the operator can speed up the floss renewal across the prongs by intensifying the pull exerted on the floss lodged between teeth.

An alternate and not illustrated process to implement the floss transfer is to impart a regular and continuous rotation in the proper direction to either one of the spools. This said rotation can be implemented for example with a transmission mechanism of gears or pulley. The transmission will pick up its rotative motion from the oscillator and convey this rotation to either one of the axes of either spool.

As the floss transfers, tension automatically builds up in the floss circuit. The first springs to be compressed are sub-tension sprigs (47), (49), (39) and (51) which are weaker than the tension breaker spring (35). It is only after the tension of the floss has overcome the tension of these four weaker springs that the floss tension can overcome the tension of the tension breaker spring (35). When the tension breaker spring (35) is overcome, the two pressure wheels (31) and (32) swing on axis (4) and cease to exert pressure against the belt (30). When the belt is no longer under tension, the transmission of rotation between the wheels is interrupted. This process frees both spools and each release an increment of floss sufficient to reduce the tension in the floss circuit and to allow the two pressure wheels to renew their pressure against the belt (30). As soon as the belt is back under tension, the floss advances and its tension is going to increase up to the point where the tension again overtakes the tension breaker spring (35). This preceeding process endlessly repeats itself.

The purpose of the sub-tension springs (47), (49), (39) and (51) is to maintain tension in the floss circuit when the disconnected spools release their floss increments. Without these said sub-tension springs, the floss would spin freely out of both spools before the tension can be reestablished by the floss advance process implied in the described embodiment.

Homogeneous maximal floss tension is obtained through endless fluctuations of tension within an established range. The maximal tension is reached when the tension breaker spring (35) is overcome by the tension of the floss circuit. The homogeneous tension is controlled by said tension breaker spring.

The maximal tension range sustained by the tension breaker spring can be controlled in a number of ways:

(a) By the manufacturer determining the strength of the tension breaker spring (35).

(b) By incorporating a means to increase or decrease the strength of the tension breaker spring 35. Such means could be a screw the user could use to tighten or loosen the tension breaker spring.

(c) By a means allowing the operator/user to interrupt on demand the transmission of rotation between the spools.

Such means could be implemented by attaching an extension to the joining bar (34) supporting the pressure wheels (31) and (32). This extension would extend outside the body frame through a corresponding opening and the user could press manually on the extension. In one direction, the manual pressure would break the tension by disconnecting the belt (30). In the opposite direction the manual pressure would bring the floss tension to a level above the resistance normally set by the tension breaker spring (35) by preventing the tension breaker spring to act; such a maneuver, by allowing the tension to continue to build up, brings the floss tension to the limit of floss strength.

The fresh floss is supplied to the consumer in a cartridge, (FIG. 8). The cartridge is positioned readily inside the body frame and over axle (22) and (27). The cartridge prevents misplacements of the spools which would make the apparatus inoperative. The transversal wall (52) that unites the spools clearly isolates the fresh floss from the used floss. The new floss is rolled up at the floss factory by conventional machinery over a polygoned shaft. The hollow polygoned shaft (23) holding fresh floss (24) becomes spool (53). Spool (53) can rotate freely at its base within the circular ring (54). The spool of fresh floss lodges into housing (55) and the cover (56) snaps on top of the housing to isolate the floss. The housing (55) has a vertical slit (57) to allow the fresh floss out of the housing. The used floss rolls up over the polygoned shaft (28), which snaps over the tip (58) of axle (27) as seen in (FIG. 6).

In (FIG. 8), polygoned shaft (28) extends outwardly above the top of housing (61). The shaft extension (59) is cut vertically by a number of vertical and tapered slits (60) that drop down inside the housing (61). Housing 61 has a vertical slit (62) to allow the used floss to enter the housing. Vertical slit (62) merges at its top with horizontal slit (63) that cuts across the ceiling of housing (61). Horizontal slit (63) allows the operator to align two diametrically opposed slits (60) with horizontal slit 63 and by this process allows the user to insert the extremity of the floss inside housing (61). When shaft (28) begins its rotation, the floss extremity automatically anchors around the shaft. This feature allows the floss to be reanchored as many times as necessary on shaft 59.

The narrower circumference in the middle part of polygoned shaft (28) lends to the gathering of the used floss in the middle section of shaft 59. This feature insures that the used floss will not roll over and cover the lower ends of the tapered slits (60) and allows for reanchoring of the floss extremity around shaft (28) should the floss be cut and after any amount of used floss has been rolled around shaft (28).

To account for variations in the height of teeth from one age group to another, the apparatus can be manufactured with prongs of different length.

The remote possibility remains that the floss could become entangled in a filling during a flossing. The continuous floss transfer and the incessant lateral motions of the floss makes it a remote possibility. In any event the remedy is to pull on the apparatus to take the headpiece out of the mouth from where the floss can easily be cut.

An alternate solution is to place emergency cutters next to the springs (47) and (49). These emergency cutters will cut loose that portion of floss extending from spring (47), through the prongs, to spring (49) allowing the user to remove the headpiece from the mouth.

The automatic flossing apparatus can be operated with or without a motor. The motor relieves the user from the obligation to initiate the oscillating motions.

In the motorless apparatus, the swing motions of the oscillator are procured manually on the tips of (6) and (7) by either a right or left handed person. The floss advance/transfer is best accomplished by immobilizing the prongs with the fingers of one hand while the floss is forced to slide over the prongs by pressing manually on tips 6 and 7 of the oscillator.

The motorless apparatus compares favorably with other apparatuses already on the market.

Exclusive of the motor and its cam drive mechanism, the apparatus can be manufactured with the same parts for both motor and motorless versions.

The language and illustrations of the preceeding presentation have been used to describe but not to limit the invention, neither have they been used to restrict the scope of the invention by excluding variations or modifications that can be made in the design and arrangement of the parts without departing from the spirit of the invention which is defined and limited only by what is now claimed.

I claim:

1. An automatic flossing apparatus having an elongated body, and having two spools, one for disbursing new floss and one for rolling up the used floss, a two prong pivotable headpiece hinged at one end of said body, an oscillator for subjecting said pivotable headpiece and floss to short back and forth motions from side to side, wherein the floss follows a circuit beginning at said spool of new floss, then to said oscillator, then across said two prongs of said pivotal headpiece, back to said oscillator, then picked up by said spool for the used floss, and tension means for maintaining tension on said floss circuit, said tension means simultaneously taking up slack caused by feeding the floss across said circuit and by the short back and forth oscillations of said pivotable headpiece.

2. An automatic flossing apparatus as in claim 1 wherein said headpiece is reversible by being tiltable up and down, whereby said headpiece can be adjusted from a downward facing position allowing easy access to the lower teeth to an upward facing position allowing easy access to the upper teeth.

3. An automatic flossing apparatus as in claim 1 wherein the force to be applied on the oscillator to cause the oscillator to oscillate and the floss to be subject to back and forth motions can be exercised alternatively by either:
   (1) lateral motions of the fingers of the operator/user applied on both or either tips of the oscillator, said tips protruding outside the side walls of the body of the apparatus, or
   (2) swing motions applied on the axis of the oscillator and generated by a motor through the action of a cam.

4. An automatic flossing apparatus as in claim 1 comprising a mechanical system to constantly increase the floss tension between the spools. Wherein the rotation of one spool is automatically transmitted to the other spool and wherein as a result of:
   (1) different spool sizes, or
   (2) changes of ratio in the parts used to transmit the rotation from one spool to the other, or
   (3) both one and two above, the spool rolling up the used floss wants to roll more floss than the disbursing spool can unwind and whereby instigating a rotative motion to unroll new floss while rolling up used floss, inevitably diminishes the floss length between the spools and therefore increases the tension in said floss circuit.

5. An automatic flossing apparatus as in claim 4 wherein the transmission of rotation from one spool to the other is achieved by a transmission mechanism composed of one or several gears, contact wheels or pullies and belts.

6. An automatic flossing apparatus as in claim 5 comprising a mechanical system to sustain the floss tension, wherein a crank or like mechanism allows the transmission of rotation of one spool to the other to take place in one intended direction causing the disbursing spool to unwind the new floss and the pick-up spool to roll up the used floss, said crank or like mechanism being attached to either spool prevents said transmission of rotation to take place opposite to the one intended direction.

7. An automatic flossing apparatus as in claim 6 comprising a mechanical system to reduce the increasing floss tension built up by the transmission of rotation between the spools, wherein whenever the increasing floss tension exceeds a level controlled by a tension release spring, said floss tension triggers a mechanism which interrupts the transmission of rotation between the spools and allows at least one spool to spin free on its axis and release an increment of floss thereby reducing the increased tension.

8. An automatic flossing apparatus as in claim 7 comprising a mechanical system to reduce the increasing floss tension built up by the transmission of rotation between the spools, wherein said transmission of rotation is achieved by one belt kept under tension by two tension wheels each one having its axis at the opposite end of an oscillating piece free to move on its pivot and wherein, said oscillating piece is subject to the pressure of a tension release spring causing the two tension wheels to press on the belt and wherein the axis of the tension wheels indirectly extend upward to become movable stakes sustaining the floss circuit under tension whereby, whenever the floss tension overcomes the resistance of said tension release spring, the axis of both said tension wheels are displaced to cease pressing agaist the belt, which in turn interrupts the transmission of rotation between the spools, which in turn allows one spool to spin free on its axis, which in turn releases an increment of floss from one of the spools, which in turn reduces the floss tension. This process can also be implemented with one tension wheel.

9. An automatic flossing apparatus as in claim 8 comprising a number of sub-tension springs to maintain sub-levels of tension in the floss circuit whenever the floss is subject to the variations of tension inherent with the hand motions of the operator/user pulling with variable strength on the floss anchored around a tooth. Said sub-levels of tension being necessary to insure that the transmission of motion of the oscillator to the headpiece is carried by the motions of the floss.

10. An automatic flossing apparatus as in claim 9 wherein the floss transfer from the disbursing spool to the pick-up spool is instigated by a discrepancy existing between the allowed arced course described by the prongs and the allowed arced course described by the oscillator, said discrepancy causing the prongs to run a shorter course than the oscillator. Whereby the oscillator by said discrepancy forces the floss to slide over the prongs with each swing while simultaneously the floss either slides over one end-guider of the oscillator or is subject to being pulled out of the spools. But since the cranked spool only allows the disbursing spool to unwind and the pick-up spool to roll up on the account of the transmission rotating both spools together, the oscillator in one swing is prevented by the crank from pulling the floss from the pick-up spool which causes the floss to slide over the end-guider of the oscillator, while in the alternate swing the crank then allows the floss to be pulled out of the disbursing spool which causes the floss to be transferred with each alternate swing from the disbursing spool to the pick-up spool by an increment equal to said discrepancy.

11. An automatic flossing apparatus as in claim 9 wherein the floss transfer between the spools is provided in this alternate process by the motions of the oscillator. Wherein each alternate swing of the oscillator is utilized to impart a rotative motion to one of the spools, said rotative motion causing the spool disbursing the new floss to unwind and consistently causing the pick-up spool to roll up the used floss.

12. An automatic flossing apparatus as in claim 1 wherein the two prongs of the headpiece are united by a slightly curved flexible rod rotating within a space comprised between the two faces of a U-shaped support, said space being so asymmetrically profiled as to force said rod to conform to said space in the position where the prongs are perpendicular to said support, wherein said perpendicular position of the prongs either upward or downward is further secured by the floss tension causing the prongs to curve toward one another and to further engage and lock into carved notches located on the edges of the hinge support. Wherein said headpiece the U-shpaed support holding the prongs swings laterally from a pivot joining the headpiece to an extension of the body of the apparatus, wherein the design of said pivotable support and a corresponding design in said extension limits the headpiece to swing within a definite arc course.

13. An automatic flossing apparatus as in claim 1 wherein the two spools are incorporated into a cartridge consisting of two housings joined by a transversal piece. One housing containing the fresh floss rolled over a hollow polygoned shaped shaft, said shaft fitting over a corresponding axle drive, said shaft turning with said axle within the housing. The fresh floss being pulled out of the housing through a vertical slit. The other housing being of a similar design stores the used floss but has a horizontal slit across the ceiling of the housing corresponding to the vertical slit in the wall of the housing and said housing is circularly opened in the middle of the ceiling to allow the centered polygoned shaped shaft to extend outwardly above the housing, while said shaft extension is cut vertically by a number of tapered slits ending below the level of the ceiling of the housing. Whereby the above described disposition the operator/user of the apparatus can reanchor as many times as necessary the end section of the used floss onto the shaft by aligning two opposed slits of the shaft extension with the horizontal slit across the ceiling of the used floss housing.

\* \* \* \* \*